United States Patent [19]

Young

[11] 4,056,611
[45] Nov. 1, 1977

[54] THERAPEUTIC COMPOSITION

[75] Inventor: Henry Y. Young, Delmar, N.Y.

[73] Assignee: Stiefel Laboratories, Inc., Oak Hill, N.Y.

[21] Appl. No.: 351,773

[22] Filed: Apr. 16, 1973

[51] Int. Cl.$^2$ .............................................. A61K 7/135
[52] U.S. Cl. ............................... 424/62; 424/DIG. 3; 424/338
[58] Field of Search .................... 424/62, DIG. 3, 338

[56] References Cited

U.S. PATENT DOCUMENTS

| | | | |
|---|---|---|---|
| 1,838,707 | 12/1931 | Rutzler, Jr. et al. | 424/338 |
| 2,218,172 | 10/1940 | Kokatnur | 424/48 |
| 2,542,898 | 2/1951 | Brown et al. | 424/338 |
| 3,530,217 | 9/1970 | White et al. | 424/338 |
| 3,535,422 | 10/1970 | Cox et al. | 424/338 |

OTHER PUBLICATIONS

Pharmaceutical Formulas, 1947, vol. 2, pp. 76 & 94, RS 125 P 45.
Pharmaceutical Formulas, 1954, vol. I, pp. 55, 845 & 853.
U.S. Dispensatory, 1955, Part I, pp. 1308-1311.

*Primary Examiner*—Dale R. Ore
*Attorney, Agent, or Firm*—Pennie & Edmonds

[57] ABSTRACT

The therapeutic composition is for the treatment of acne and comprises a stable dispersion of finely divided particles of benzoyl peroxide in an aqueous alcohol vehicle having a single phase, said phase being non-lipid and containing a non-ionic surface active agent that is soluble in the aqueous alcohol vehicle of the composition. The composition comprises from about 1 to 30 percent by weight benzoyl peroxide, from about 1 to 30 percent by weight of said surface active agent, from about 10 to 80 percent by weight of an alkyl alcohol having from 1 to 3 carbon atoms, and from about 10 to 80 percent by weight of water. The hydrophilic portion of the surface active agent is a polyoxyalkylene moiety wherein each oxyalkylene group contains from 2 to 3 atoms, and preferably is polyoxyethylene lauryl ether.

9 Claims, No Drawings

THERAPEUTIC COMPOSITION

BACKGROUND OF THE INVENTION

1. Field of the Invention

This invention relates to therapeutic compositions for the treatment of acne and in particular to those compositions which contain benzoyl peroxide.

2. Prior Art

Acne and seborrhea are conditions of the human skin characterized by an excessive flow of sebum, or skin oil, from the sebaceous glands which are located in the pilosebaceous apparatus. The channel through which sebum reaches the skin surface is the duct of the hair follicle. The presence of excessive amounts of sebum in the duct and on the skin acts to block or stagnate the continuous flow of sebum from the follicular duct, thus producing a thickening of the sebum which becomes a solid plug known as a comedone. When this occurs, hyperkeratinization of the follicular opening is stimulated, thus completely closing the duct. The usual result is a papule, a pustule, or a cyst, often contaminated with bacteria which cause secondary infections. These occurences characterize the disease state known as acne, and in lesser severity, seborrhea.

Many topical therapeutic agents are employed in the treatment of acne and seborrhea to prevent the blocking of the follicular duct, to reopen the duct once it has become blocked, to act against the infecting bacteria or the thickened sebum, or to provide combinations of each of these actions. The horny outer layer of the skin is formed of dead cells composed largely of a substance known as keratin, and therapeutic agents which act to prevent the blocking of the follicular duct by promoting the removal or scuffing off of excess keratin are known as keratolytic agents. For example, the use of sulfur as a mild cutaneous irritant to remove the horny layer of skin, and with it the debris clogging the follicular openings, is well known in the art.

Benzoyl peroxide $(C_6H_5CO)_2O_2$, is a colorless, odorless, tasteless, crystalline solid that is stable at ordinary room temperatures but which is flammable and is capable of exploding when confined and subjected to grinding, heat or flame. It is a powerful oxidizing agent completely non-toxic to man, and because of its lack of local injurious effects and its lack of penetration into tissue with consequent protein precipitation, it has heretofore been proposed that benzoyl peroxide be employed as an antibacterial and keratolytic agent in the treatment of acne, and extensive clinical evaluation of this substance has conclusively demonstrated its effectiveness for this purpose.

Finely divided benzoyl peroxide is advantageously incorporated in a cream or ointment for convenience in applying it to the skin. However, because of the powerful oxidizing properties of benzoyl peroxide, the inclusion of this substance in conventional ointment or cream bases results in unstable compositions that soon display an unacceptable loss in keratolytic potency. A stable benzoyl peroxide composition that is very effective in the treatment of acne and that has a projected shelf life of over eight years is described in U.S. Pat. No. 3,535,422 to Cox and Cuifo. The Cox and Cuifo composition comprises a uniform dispersion of finely divided benzoyl peroxide particles in an emulsion of water and certain selected organic emollients. An oil and water emulsion is, by definition, a system having at least two liquid phases, and it usually comprises an oil-in-water system in which a continuous aqueous phase has dispersed therein minute droplets of a discontinuous lipid phase. When the composition is applied to the patient's skin the water content of the emulsion evaporates leaving most of the organic emollients and the benzoyl peroxide particles on the surface of the skin near and in contact with the acne sites.

After an intensive investigation of the problems involved in formulating effective and stable benzoyl peroxide-containing compositions for the treatment of acne, I have discovered and developed a composition containing benzoyl peroxide that is significantly more effective in the treatment of acne than any benzoyl peroxide-containing composition previously known in the art. My new composition employs an aqueous alcohol vehicle having a single phase that is non-lipid and that contains a non-ionic surface active agent that is soluble in the aqueous alcohol vehicle. The effectiveness of the composition appears to be due to the extremely fine particle size of the benzoyl peroxide employed, to the presence of the non-ionic surface active agent which removes skin oil from the acne sites and thereby allows the benzoyl peroxide to intimately contact and penetrate the sites, and to the absence of lipids which might otherwise inhibit the antiseptic and keratolytic activity of the benzoyl peroxide.

SUMMARY OF THE INVENTION

My new therapeutic composition for the treatment of acne comprises a stable dispersion of finely divided particles of benzoyl peroxide in an aqueous alcohol vehicle having a single phase. The single phase of the composition is non-lipid and contains a non-ionic surface active agent that is soluble in the aqueous alcohol vehicle of the composition. The composition contains from about 1 to 30 percent, and preferably from 5 to 15 percent, by weight of benzoyl peroxide having a particle size of less than 100 microns, for about 1 to 30 percent, and preferably from 5 to 15 percent, by weight of the surface active agent, from about 10 to 80% by weight of an alkyl alcohol having from 1 to 3 carbon atoms, and from about 10 to 80 percent by weight of water. The hydrophilic portion of the surface active agent is a polyoxyalkylene moiety wherein each oxyalkylene group contains from 2 to 3 carbon atoms, and advantageously the surface active agent is polyoxyethylene lauryl ether. The composition also advantageously contains minor amounts of a suspending agent (for example, colloidal magnesium aluminum silicate) for maintaining the dispersed particle of benzoyl peroxide in suspension in the aqueous alcohol vehicle and a viscosity builder (for example, hydroxypropylmethylcellulose) for imparting a desired consistency to the composition.

DETAILED DESCRIPTION

The composition of the invention must contain sufficient benzoyl peroxide to be therapeutically effective, and should not contain more peroxide than can be uniformly dispersed in the vehicle to form a smoothly spreadable composition. These considerations dictate that the composition contain at least about 1% and not more than about 30% by weight benzoyl peroxide, and we presently prefer that the composition contain from about 5 to about 15% by weight benzoyl peroxide. The benzoyl peroxide constituent of the composition should be of high purity (that is, in the order of $98 \pm 1\%$ $(C_6H_5CO)_2O_2$) and in the form of relatively finely divided crystalline particles. High purity benzoyl peroxide in the form of dry crystals having a particle size such that at least 99% will pass through a 60 mesh screen (Tyler Standard) is available commercially, and this form of the peroxide can be blended directly with the other constituents of the composition. However, I presently prefer to employ a somewhat more coarsely crystalline form of benzoyl peroxide that is packaged wet with water, a fact which greatly increases the safety with which the peroxide can be handled. The wet packed peroxide is dustless, free flowing and disperses readily in the fluid medium comprising the balance of the composition. The various ingredients of the composition are thoroughly blended together, and the particles of crystalline benzoyl peroxide are simultaneously physically reduced in size, by milling the mixture to obtain a finished composition containing finely divided benzoyl peroxide having a particle size of less than 100 microns pursuant to the practice of the invention.

The base in which the finely divided benzoyl peroxide is dispersed comprises an aqueous alcohol vehicle having a single phase. The single phase of the aqueous alcohol vehicle is non-lipid and contains a non-ionic surface active agent that is soluble in the aqueous alcohol vehicle. The composition also advantageously contains minor amounts of a suspending agent for maintaining dispersed particles of benzoyl peroxide in suspension in the aqueous alcohol vehicle and a viscosity builder for imparting a desired consistency to the composition. In addition, the composition advantageously contains a small amount of an essence which imparts a pleasing fragrance to the composition. The relative portions of benzoyl peroxide, water, alcohol, surface active agent and other ingredients in the composition will depend upon the desired therapeutic potency or activity of the composition and upon the desired physical characteristics (for example, viscosity) of the composition. As the result of my investigations, I have found that the composition should contain from about 1 to 30%, and preferably from 5 to 15% by weight of benzoyl peroxide, from about 10 to 80% by weight of water, from about 10 to 80% by weight of an alkyl alcohol having from 1 to 3 carbon atoms, from about 1 to 30%, and preferably from 5 to 15%, by weight of the surface active agent, and advantageously from 0.1 to 7.5% by weight of a suspending agent and from about 0.1 to 7.5% by weight of a viscosity builder.

The alcohol employed in the aqueous alcohol vehicle must be soluble in water and it must be relatively volatile so that it will not leave any lipid residue on the skin. The alcohol content of the aqueous alcohol vehicle serves as a co-solvent for the surface active agent in the vehicle and also as an antiseptic and drying agent when applied to the skin. Alkyl alcohols having from 1 to 3 carbon atoms meet the foregoing criteria and are used in the formulation of the composition of the invention. As noted, the composition from about 10 to 80% by weight of one or more of these alcohols, the amount of alcohol present in the aqueous alcohol vehicle of the composition being sufficient insure that the surface active agent will dissolve therein.

The surface active agent employed in the composition must be non-ionic and must be soluble in the aqueous alcohol vehicle. When applied to the skin the surface active agent helps remove sebum and other oily substances from the skin and hair follicles, thereby allowing the benzoyl peroxide content of the composition to intimately contact the skin and acne sites. It also serves as a carrier or vehicle for the transport of the benzoyl peroxide particles to the acne sites. As noted, the composition may contain from 1 to 30% by weight of the surface active agent, and preferably it contains from 5 to 15% by weight of this substance. The hydrophilic portion of the surface active agent advantageously is a polyoxyalkylene moiety, each oxyalkylene group of which contains from 2 to 3 carbon atoms. That is to say, the polyoxy alkylene moiety of the surface active agent is polyoxyethylene or polyoxypropylene. Non-ionic surface active agents useful in the practice of the invention include, but are not limited to, polyoxyethylene lauryl ether, polyoxyethylene stearate, polyoxyethylene sorbitan monolaurate, polyethylene glycol laurate, polyoxyethylene sorbitan monopalmitate, polyoxyethylene oleyl ether and polyoxypropylenepolyoxyethylene polymer. Of the non-ionic surface active agents which meet the foregoing criteria I presently prefer to use polyoxyethylene lauryl ether.

The composition advantageously contains from about 0.1 to 7.5% by weight of a suspending agent the function of which is to maintain the dispersed particles of benzoyl peroxide in suspension in the aqueous alcohol vehicle, and it also advantageously contains from about 0.1 to 7.5% by weight of a viscosity builder the function of which is to impart the desired consistency to the composition. A variety of suspending agents and viscosity builders are known to be useful in the formulation of pharmaceutical products, and the selection of a particular suspending agent and/or viscosity builder from among all those of known utility in the pharmaceutical art is a matter within the skill of an experienced formulator of pharmaceutical preparations. By way of example, the suspending agent may be either an organic or an inorganic substance of which carboxy vinyl polymer and colloidal magnesium aluminum silicate is a representative example, respectively. Similarly, viscosity builders include but are not limited to natural gums, modified starch and chemically modified cellulose of which a particularly advantageous viscosity builder is hydroxypropylmethyl cellulose. If desired, minute amounts of a compatible acid or base may be added to the composition to adjust the relative acidity or alkalinity thereof, the pH of the composition usually being adjusted to be within the range of 2.5 and 7.0. In addition, a minute amount of an essence or fragrance may be added to the composition to impart a pleasant fragrance thereto.

The following examples are representative but not limitative of therapeutic composition prepared in accordance with the invention.

EXAMPLE I 5,581 parts by weight of purified water were heated to 70° C., and then 250 parts by weight of colloidal magnesium aluminum silicate were added to the hot water while stirring the water. Stirring of the hot aqueous mixture was continued for 1½ hours, and then 150 parts by weight of hydroxypropylmethylcellulose were added thereto with continued stirring for an additional 15 minutes. The aqueous mixture was cooled to 50° C., and then 300 parts by weight of polyoxyethylene (9) lauryl ether were added thereto. Stirring of the mixture was continued while it was being cooled to 35° C. whereupon 3000 parts by weight of ethyl alcohol, 5 parts by weight of citric acid and 714 parts by weight of wet pack benzoyl peroxide (70% benzoyl peroxide-30% water) were added to the aqueous mixture. Stirring of the mixture was continued for 10 more minutes and then the mixture was milled to obtain a smooth suspension of finely divided benzoyl peroxide in an aqueous alcohol vehicle, the benzoyl peroxide having a particle size of less than 100 microns. The finished product had the following composition:

| | |
|---|---|
| Benzoyl peroxide | 5.00 % by weight |
| Water | 57.95 % by weight |
| Ethyl alcohol | 30.00 % by weight |
| Polyoxyethylene (9) lauryl ether | 3.00 % by weight |
| Colloidal magnesium aluminum silicate | 2.50 % by weight |
| Hydroxypropylmethylcellulose | 1.50 % by weight |
| Citric acid | 0.05 % by weight |

Other examples of the composition of the invention are:

EXAMPLE 2

| | |
|---|---|
| Benzoyl peroxide | 5.46 % by weight |
| Water | 40.69 % by weight |
| Ethyl alcohol | 44.10 % by weight |
| Polyoxyethylene (12) lauryl ether | 6.00 % by weight |
| Colloidal magnesium aluminum silicate | 2.50 % by weight |
| Hydroxypropylmethylcellulose | 1.00 % by weight |
| Citric acid | 0.05 % by weight |
| Essence | 0.20 % by weight |

EXAMPLE 3

| | |
|---|---|
| Benzoyl peroxide | 2.50 % by weight |
| Water | 11.55 % by weight |
| Ethyl alcohol | 70.00 % by weight |
| Polyoxyethylene (8) stearate | 15.00 % by weight |
| Carboxy vinyl polymer | 0.50 % by weight |
| Hydroxypropylcellulose | 0.45 % by weight |

EXAMPLE 4

| | |
|---|---|
| Benzoyl peroxide | 2.0 % by weight |
| Water | 16.8 % by weight |
| Ethyl alcohol | 70.0 % by weight |
| Polyoxyethylene (12) lauryl ether | 10.0 % by weight |
| Carboxy vinyl polymer | 1.0 % by weight |
| Potassium hydroxide | 0.2 % by weight |

EXAMPLE 5

| | |
|---|---|
| Benzoyl peroxide | 15.00% by weight |
| Water | 49.35% by weight |
| Ethyl alcohol | 25.00% by weight |
| Polyoxyethylene (40) stearate | 8.50% by weight |
| Colloidal magnesium aluminum silicate | 1.50% by weight |
| Sodium carboxymethylcellulose | 0.60% by weight |
| Citric acid | 0.05% by weight |

EXAMPLE 6

| | |
|---|---|
| Benzoyl peroxide | 5.00% by weight |
| Water | 76.97% by weight |
| Isopropyl alcohol | 10.00% by weight |
| Polyoxyethylene (20) sorbitan Monolaurate | 5.00% by weight |
| Hydroxypropylmethylcellulose | 1.50% by weight |
| Xanthan gum | 1.50% by weight |
| Phosphoric acid | 0.03% by weight |

EXAMPLE 7

| | |
|---|---|
| Benzoyl peroxide | 3.00% by weight |
| Water | 68.94% by weight |
| Ethyl alcohol | 15.00% by weight |
| Polyoxypropylenepolyoxyethylene polymer | 10.00% by weight |
| Hydroxypropylmethylcellulose | 1.50% by weight |
| Guar gum | 1.50% by weight |
| Tartaric acid | 0.06% by weight |

EXAMPLE 8

| | |
|---|---|
| Benzoyl peroxide | 15.00% by weight |
| Water | 46.93% by weight |

EXAMPLE 8-continued

| | |
|---|---|
| Ethyl alcohol | 15.00% by weight |
| Polyethylene glycol 400 laurate | 20.00% by weight |
| Hydroxyethylcellulose | 2.50% by weight |
| Sodium carboxymethylcellulose | 0.50% by weight |
| Citric Acid | 0.07% by weight |

EXAMPLE 9

| | |
|---|---|
| Benzoyl peroxide | 25.0 % by weight |
| Water | 41.3 % by weight |
| Isopropyl alcohol | 10.0 % by weight |
| Polyoxyethylene (20) sorbitan monopalmitate | 20.0 % by weight |
| Sodium carboxymethylcellulose | 1.5 % by weight |
| Sodium naphthalene sulfonic acid-formaldehyde condensate | 2.0 % by weight |
| Citric acid | 0.2 % by weight |

EXAMPLE 10

| | |
|---|---|
| Benzoyl peroxide | 7.50 % by weight |
| Water | 62.95 % by weight |
| Isopropyl alcohol | 15.00 % by weight |
| Polyoxyethylene (20) oleyl ether | 3.00 % by weight |
| Colloidal magnesium aluminum silicate | 1.00 % by weight |
| Polyethylene glycol polymer | 10.50 % by weight |
| Citric acid | 0.05 % by weight |

EXAMPLE 11

| | |
|---|---|
| Benzoyl peroxide | 10.99 % by weight |
| Water | 35.16 % by wight |
| Ethyl alcohol | 44.10 % by weight |
| Polyoxyethylene (12) lauryl ether | 6.00 % by weight |
| Colloidal magnesium aluminum silicate | 2.50 % by weight |
| Hydroxypropylmethylcellulose | 1.00 % by weight |
| Citric acid | 0.05% by weight |
| Essence | 0.20 % by weight |

The composition is applied topically to the skin of the patient by rubbing the benzoyl peroxide-containing product onto the areas being treated one or more times daily, and advantageously at least once a day at bedtime. The aqueous alcohol content of the composition quickly evaporates leaving a non-lipid benozyl peroxide residue on the skin near and at the acne sites. After a few days a generalized peeling and desquamation of the skin occurs in the treated areas. Almost all persons who use the composition in this manner show a definite suppression of their acne eruption within the first few weeks of treatment. Moreover, the composition of the invention has been demonstrated to be markedly more effective and faster acting than benzoyl peroxide-containing emulsion compositions of comparable strength previously known in the art.

Clinical evidence has shown that a composition formulated in accordance with the invention and containing 5% benzoyl peroxide (specifically, the composition of Example 2 above) is therapeutically superior to a conventional emulsion-type composition containing 10% benzoyl peroxide. In a comparative investigation employing the "double blind" procedure, 25 acne patients were treated with the conventional emulsion-type composition containing 10% benzoyl peroxide (10% BPO) and 27 acne patients were treated with the composition of the invention containing 5% benzoyl peroxide (5% BPO). The compositions were applied twice daily and the improvement or suppression of the acne eruptions were observed and recorded. Categories of improvement were designated as follows:

TABLE 1

| | |
|---|---|
| Excellent | 75% or better reduction in lesion count |
| Good | 50% or better reduction in lesion count |

TABLE 1-continued

| | |
|---|---|
| Fair | 25% or better reduction in lesion count |
| Poor | less than 25% reduction in lesion count |

On completion of the double blind study the following results were observed:

TABLE 2

| | 5% BPO Composition of the Invention | 10% BPO Prior Art Composition |
|---|---|---|
| Excellent | 9 patients | 2 patients |
| Good | 14 patients | 8 patients |
| Fair | 2 patients | 10 patients |
| Poor | 2 patients | 5 patients |

From the foregoing description of the acne treatment composition of the invention, and in particular from the results of the above-described clinical investigation, it will be seen that I have made an important contribution to the art to which the invention relates.

I claim:

1. A therapeutic composition for the treatment of acne consisting of a stable dispersion of finely divided particles of benzoyl peroxide in an aqueous alcohol vehicle, said aqueous alcohol vehicle being a single non-lipid phase consisting essentially of a solution of water and an alkyl alcohol having from 1 to 3 carbon atoms and in which solution is dissolved a non-ionic surface active agent, the hydrophilic portion of which is a polyoxyalkylene moiety wherein each oxyalkylene group contains from 2 to 3 carbon atoms, said surface active agent being soluble in said solution, said composition containing from about 1 to 30 percent by weight benzoyl peroxide having a particle size of less than 100 microns, from about 1 to 30 percent by weight of a surface active agent, from about 10 to 80 percent by weight of said alkyl alcohol, and from about 10 to 80 percent by weight of water.

2. The composition according to claim 1 in which the hydrophilic portion of the surface active agent is polyoxyethylene moiety.

3. The composition according to claim 1 in which the hydrophilic portion of the surface active agent is polyoxypropylene moiety.

4. The composition according to claim 1 in which the surface active agent is polyoxyethylene lauryl ether.

5. The composition according to claim 1 in which the composition contains from about 0.1 to 7.5 percent by weight of a viscosity builder selected from the group consisting of natural gums, modified starch and chemically modified cellulose.

6. The composition according to claim 1 comprising essentially 5.0% by weight benzoyl peroxide, 30.0% by weight ethyl alcohol, 3.0% by weight polyoxyethylene lauryl ether, 2.5% by weight colloidal magnesium aluminum silicate, 1.5% by weight hydroxypropylmethylcellulose, 0.05% by weight citric acid and the balance water.

7. The composition according to claim 1 comprising essentially about 5% by weight benzoyl peroxide, about 40% by weight ethyl alcohol, about 6% by weight polyoxyethylene lauryl ether, about 2.5% by weight colloidal magnesium aluminum silicate, about 1.5% by weight hydroxypropylmethylcellulose, about 0.05% by weight citric acid and the balance water.

8. The composition according to claim 1 comprising essentially 10.99% by weight benzoyl peroxide, 44.10% by weight ethyl alcohol, 6.0% by weight polyoxyethylene lauryl ether, 2.5% by weight colloidal magnesium aluminum silicate, 1.0% by weight hydroxypropylmethylcellulose, 0.05% by weight citric acid and the balance water.

9. The composition according to claim 1 comprising essentially about 10% by weight benzoyl peroxide, about 40% by weight ethylalcohol, about 6% by weight polyoxyethylene lauryl ether, about 2.5% by weight colloidal magnesium aluminum silicate, about 1% by weight hydroxypropylmethylcellulose, about 0.05% by weight citric acid and the balance water.

* * * * *